(12) United States Patent
Bezzola

(10) Patent No.: US 7,354,552 B2
(45) Date of Patent: Apr. 8, 2008

(54) GAS CHROMATOGRAPH WITH FLAME IONISATION DETECTOR FOR PARALLEL HYDROCARBON ANALYSIS

(75) Inventor: Carlo Bezzola, Milan (IT)

(73) Assignee: Geolog S.p.A., Potenza (IT)

( * ) Notice: Subject to any disclaimer, the term of this patent is extended or adjusted under 35 U.S.C. 154(b) by 804 days.

(21) Appl. No.: 10/481,562

(22) PCT Filed: Dec. 13, 2001

(86) PCT No.: PCT/EP01/14677

§ 371 (c)(1),
(2), (4) Date: Dec. 22, 2003

(87) PCT Pub. No.: WO03/001196

PCT Pub. Date: Jan. 5, 2003

(65) Prior Publication Data

US 2004/0234414 A1 Nov. 25, 2004

(30) Foreign Application Priority Data

Jun. 22, 2001 (IT) .................. MI2001A001329

(51) Int. Cl.
*G01N 33/00* (2006.01)

(52) U.S. Cl. ..................... 422/54; 422/50; 422/83; 422/89; 422/93

(58) Field of Classification Search .................. 422/50, 422/83, 89, 54, 93
See application file for complete search history.

(56) References Cited

U.S. PATENT DOCUMENTS 3,790,348 A 2/1974 Bossart et al.

FOREIGN PATENT DOCUMENTS

| DE | 41 36 413 | | 5/1993 |
|---|---|---|---|
| DE | 4136413 | * | 5/1993 |

OTHER PUBLICATIONS

Database WPI Section Ch, Week 198946 Derwent Publications Ltd., London, GB; Class E19, AN 1989-336224 XP002902577 & JP 01 250859 A (Shimadzu Seisakusho KK), Oct. 5, 1989.
Database WPI Section Ch, Week 199221 Derwent Publications Ltd., London, GB; Class E19, AN 1992-172690 XP002902576 & JP 04 110768 A (Shimadzu Corp), Apr. 13, 1992.

* cited by examiner

*Primary Examiner*—Jill Warden
*Assistant Examiner*—Samuel P Siefke
(74) *Attorney, Agent, or Firm*—Young & Thompson

(57) ABSTRACT

A field flame ionisation gas chromatograph for the analysis of a hydrocarbon gas mixture found in particular in mud from oil drilling and sampled by a gas carrier, which is characterised by the fact that it includes a first and a second analysis unit working in parallel simultaneously, the first analysis unit being dedicated exclusively to the analysis of methane and ethane.

16 Claims, 5 Drawing Sheets

GAS CHROMATOGRAPH WITH FLAME IONISATION DETECTOR FOR PARALLEL HYDROCARBON ANALYSIS

This invention refers to a field flame ionisation gas chromatograph for the analysis of a hydrocarbon gas mixture found in particular in mud from oil drilling. The gas mixture under analysis is usually composed of air, light hydrocarbons such as methane and ethane, and heavier hydrocarbons, all in varying concentrations.

Most field gas chromatographs known to date which are used to analyse hydrocarbon gas mixtures found in mud from oil drilling include a system of chromatographic separation columns arranged in sequence by which the hydrocarbon components of varying molecular weight present in the gas mixture flow at different speeds according to their affinity to the chromatographic material contained in the separation columns they cross, thus emerging from the last separation column in increasing molecular weight order.

The concentration of each component is measured by a flame ionisation detector (from now on called "FID") found downstream of the last column.

An electrometer converts the electric current from the FID into a voltage signal which then produces a chromatogram made up of as many peaks as the separated hydrocarbons, the area found under each of these peaks being proportional to the concentration of the relative hydrocarbon component.

During hydrocarbon research drilling, chromatographic analysis is correlated to a particular drilling depth from which the gas being examined has escaped.

Today's high drilling speeds have determined a reduction in analysis cycle times such as to allow the resolution to remain unvaried in terms of number of chromatographs carried out per drilled depth unit.

With short chromatographic analysis cycles it is difficult to distinguish chromatograph peaks registered by the flame ionisation detector upon arrival of methane and ethane components, as they tend to overlap, especially if the methane-ethane concentration ratio in the gas mixture is high.

In several traditional field flame ionisation gas chromatographs for the analysis of hydrocarbons it is also possible to obtain a linear response of the machine in a short analysis cycle only for a total hydrocarbon concentration in the gas mixture below a certain maximum value above which the machine is over-saturated. One of the most commonly used solutions to this problem is the dilution of the sample in air before analysis using the FID, which can give, errors in the constant check of the dilution.

The aim of this invention is therefore to provide a field flame ionisation gas chromatograph for the analysis of a hydrocarbon gas mixture found in particular in mud from oil drilling capable of carrying out a short and precise analysis cycle even when in presence of a high methane-ethane ratio in the gas mixture. Another objective of this invention is to create a field flame ionisation gas chromatograph for the analysis of a hydrocarbon gas mixture found in particular in mud from oil drilling capable of responding linearly both in presence of concentrations of few parts per million (ppm for short) up to a total concentration of hydrocarbons present in the gas mixture to be analysed of 100%.

These aims are reached by a field flame ionisation gas chromatograph for the analysis of a hydrocarbon gas mixture found in particular in mud from oil characterised by the fact that it comprises a first analysis unit comprising a first chromatographic column separation group connected to a relative first flame ionisation device for the chromatographic analysis of methane and ethane components of the gas mixture, and a second analysis unit working in parallel simultaneously to the first analysis unit which comprises a second chromatographic column separation group connected to a relative second flame ionisation device for the chromatographic analysis of other heavier hydrocarbon components of the gas mixture.

Since the gas chromatograph carries out the analysis of methane and ethane in the first unit and the analysis of methane, ethane and of the other hydrocarbon components in the second unit simultaneously, the first analysis unit has the total analysis cycle time available to analyse only the gas mixture's methane and ethane components, such that the moments in which the methane and ethane arrive at the first analysis unit's FID combustion chamber can be spaced out to allow a true distinction between the chromatographic peaks independently from their concentration ratio in the gas mixture. This then allows to distinguish methane concentrations of up to 100% in volume and ethane concentrations of up to few parts per million in a gas mixture.

The efficiency of separating the various molecular weight hydrocarbon components can be improved by using hydrogen ($H_2$) instead of air as carrier of the gas through every chromatographic column separation group.

The migration speed regulation of each hydrocarbon component of the mixture through each chromatographic column separation group determines the retention time of the various hydrocarbon components present in the mixture, namely the time of arrival of the mixture's hydrocarbon components to the flame ionisation detector's combustion chamber. In order to reproduce the retention times of the mixture's various hydrocarbon components the gas carrier's capacity must be kept constant.

The machine is equipped with a membrane sampling valve to sample in a reproducible way a constant volume of even a few microlitres of the gas mixture to be analysed.

The possibility of distinguishing precisely the chromatographic peaks of all the hydrocarbon components found in the gas mixture independently from the concentration in which they are present in the mixture, the high efficiency of separation between the hydrocarbon components of the gas mixture carried out by each one of the chromatograph column groups, and the possibility of sampling such small but constant and reproducible volumes of the gas mixture, all contribute to obtaining a linear answer from the machine to the various hydrocarbon component concentrations in the gas mixture without any saturation phenomenon taking place in case of extremely high concentrations of hydrocarbon components in the gas mixture.

These and other aspects will be cleared further by the description which follows of a preferred mode of execution of this invention, to be read by way of an example but not restrictive of the more general principle being claimed.

The description that follows refers to the figures attached, in which.

Figure 1A:
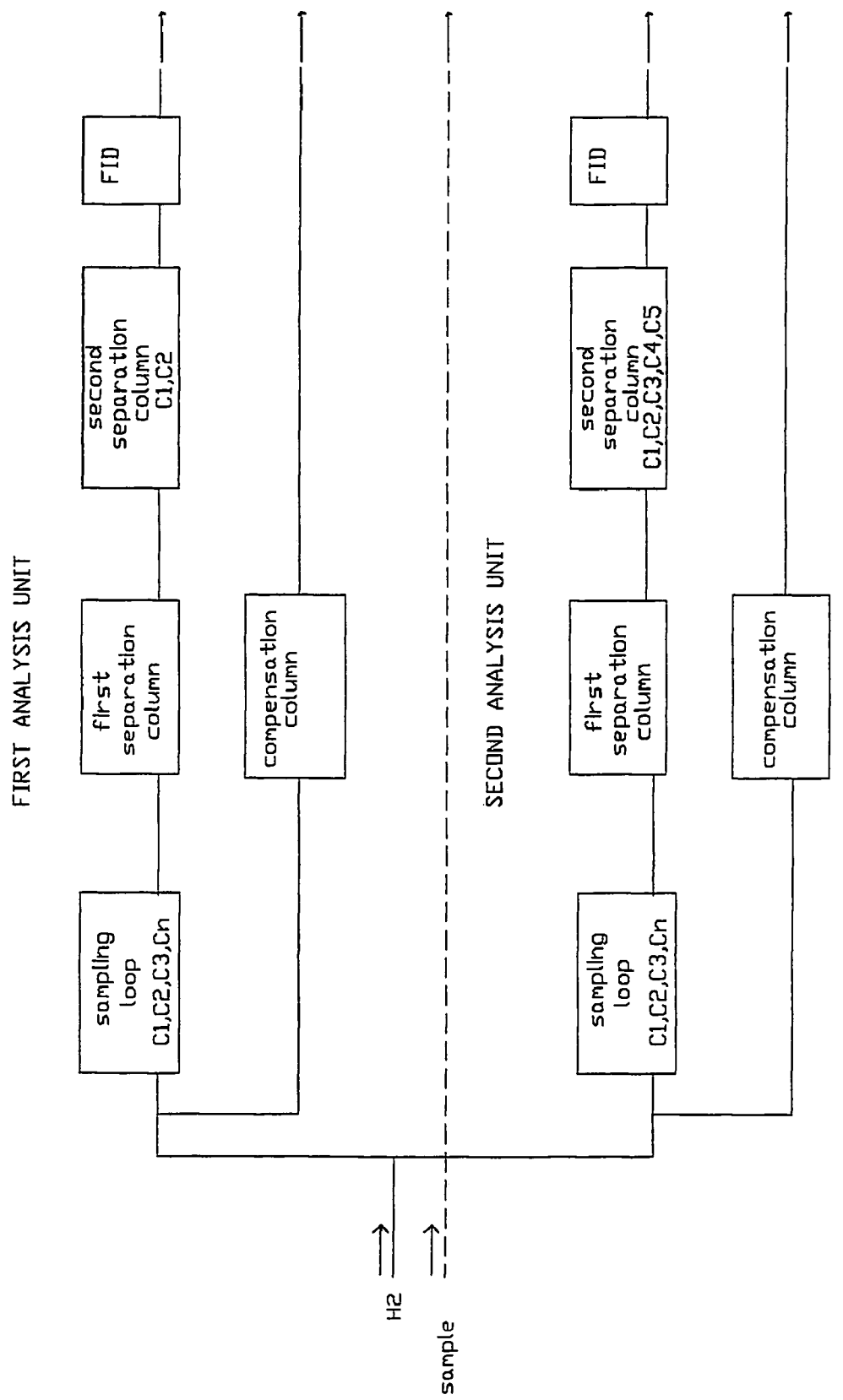
FIG. 1a is a flowchart regarding the operation of the gas chromatograph object of this invention in the so-called sampling/pre-cut phase, in which Cn indicates the hydrocarbon component having a molecule composed of n carbon atoms.
Figure 1B:
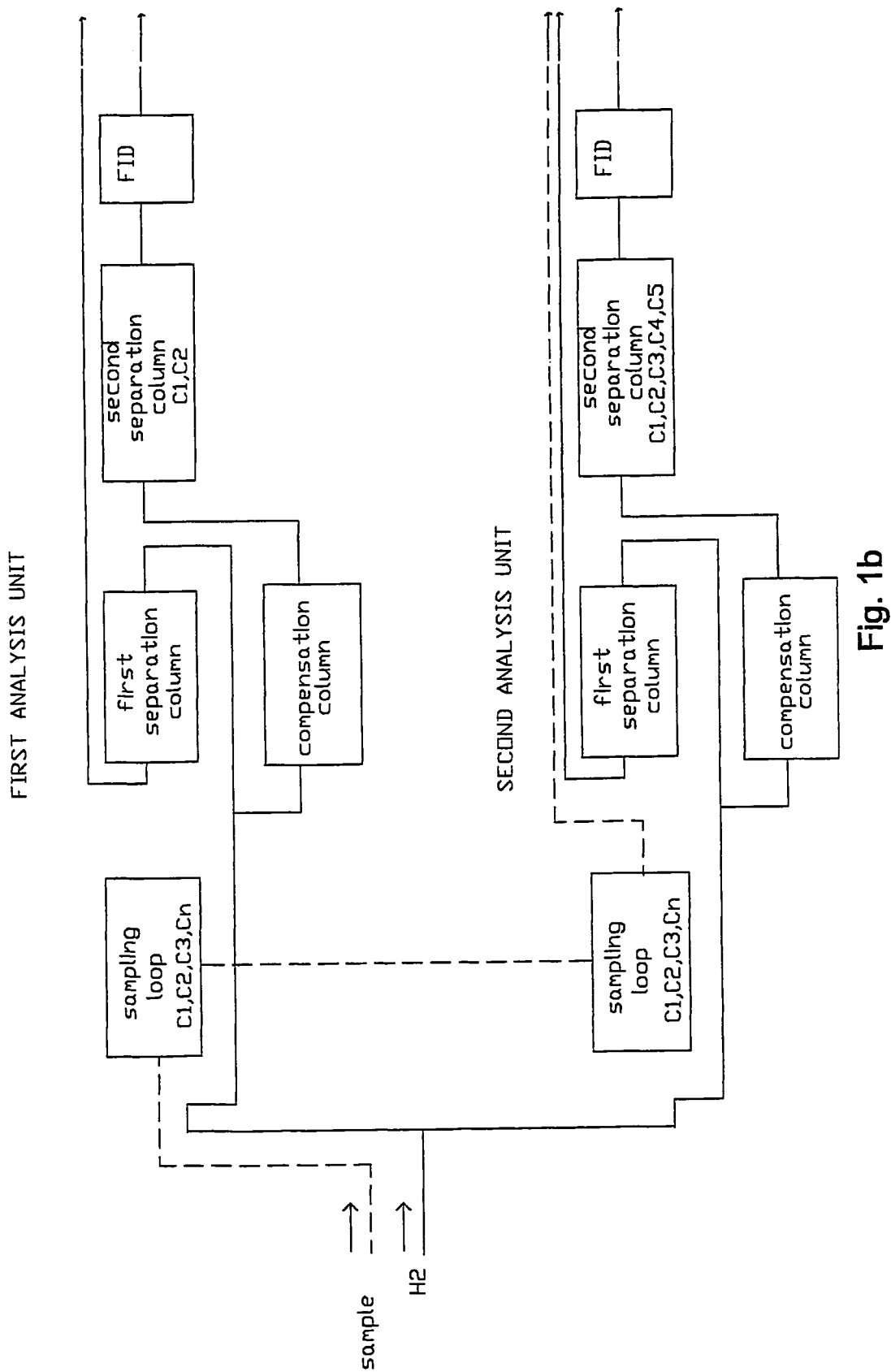
FIG. 1b is a flowchart regarding the operation of the gas chromatograph object of this invention in the so-called analysis/back-purging phase.
Figure 2:
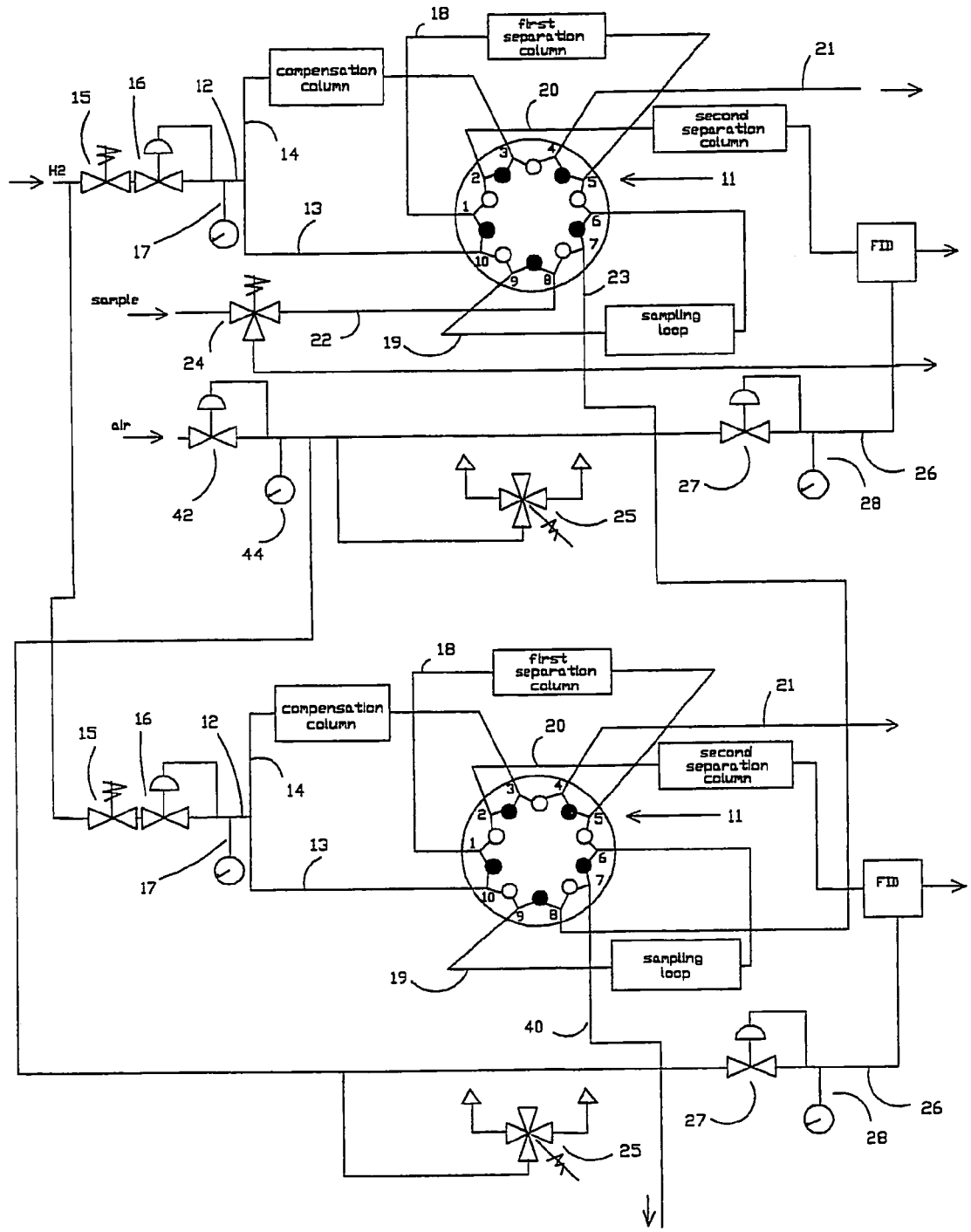
FIG. 2 is a diagram of the analytical double circuit of this invention with the sampling valve commuted on the sampling/pre-cut phase.

With reference to FIGS. 1a, 1b and 2, the gas chromatograph carries out an analysis cycle with a double analysis circuit and is therefore composed of two analysis units which operate in parallel simultaneously, the first unit being for (the analysis of methane (C1) and ethane (C2) hydrocarbon components contained in the gas mixture and the second for the analysis of heavier hydrocarbons.

The analytical circuit of each analysis unit includes: a sampling chamber (called "sample loop") from which the gas mixture sample containing air and hydrocarbon components is taken by a carrier gas; a sample valve with a ten port membrane capable of sampling a precise volume of the gas mixture to be sent to a chromatographic column separation group; a chromatographic column separation group with a thermostat set on approximately 60° C. in order to avoid condensation of the hydrocarbon components of the gas mixture, including a first separation column made up of a small steel pipe wound in a spiral, a compensation column identical to the first separation column and a second separation column, also made up of a small steel pipe wound in a spiral; a flame ionisation detector (called "FID") which is connected directly to the second separation column; and an electrometer which converts the current collected from the FID into a voltage signal which then originates a chromatogram.

The FID is an organic compound detector based on the fact that the oxidation reaction of carbon exposed to a hydrogen flame produces many ions later retrieved by an electric field and sent to the electrometer for the elaboration of the chromatogram.

The first column, the second column and the compensation column of the first analysis unit are filled with polymers of active bodies, whereas the first column, the second column and the compensation column of the second analysis unit are filled with diatomite siliceous sand impregnated of silicon oil.

By way of an example the first separation column and the compensation column of the two analysis units are 40 cm long with an internal diameter of 3 mm, the second separation column of the two analysis units is 60 cm long with an internal diameter of 3 mm.

The gas carrier is hydrogen (H2) preferably, which, thanks to its low molecular weight compared to air allows the attainment of an increased efficiency in the separation of hydrocarbon components through the chromatographic column separation group.

The sample valves indicated by 11 in FIG. 2, have ten ports indicated from 1 to 10, and can be switched between two operational conditions corresponding to two distinct phases of the analysis cycle of the double analysis circuit.

In the first switching state of the 11 sample valves the following ports are in fluid communication in pairs: 1 and 2, 3 and 4, 5 and 6, 7 and 8, 9 and 10, whereas in the second operational condition the following ports are in fluid communication in pairs: 2 and 3, 4 and 5, 6 and 7, 8 and 9, 10 and 1.

FIG. 2 shows the first analysis unit at the top and the second analysis unit at the bottom. The corresponding parts of the two analysis units are indicated using the same reference number.

The conveying circuit of the gas carrier to the sample valve 11 of each analysis unit includes a first leg 12 which has a feed opening for the carrier gas and which ends with a branch point from which a second 13 and a third 14 branch stem out.

The first branch 12 of the carrier gas' conveying circuit is fitted with, in series, from upstream to downstream with reference to the carrier gas feeding direction, a solenoid valve 15 intercepting the carrier gas flow, a pressure regulator 16 of the carrier gas, and a pressure gauge 17 to read the carrier gas' pressure.

The second branch 13 of the conveying circuit of the carrier gas is connected to the port 10 of the sample valve 11.

The third branch 14 of the circulation circuit of the carrier gas is connected to the port 3 of the sample valve 11 and is the compensation column.

A connection between the port 1 and the port 5 of the sample valve 11 is the first separation column 18.

A connection between port 6 and port 9 of the sample valve is the sample loop 19.

A connection between port 2 of the sample valve 11 and the flame ionisation detector (FID) is the second separation column 20.

A pipeline 21 connects port 4 of the sample valve 11 to an exit pipe.

The sample circulation circuit includes a branch 22 which has a feeding opening of the sample and a discharge connected to the port 8 of the sample valve 11 of the first analysis unit, a branch 23 connecting the port 7 of the sample valve 11 of the first analysis unit to the exit 8 of the sample valve 11 of the second analysis unit, and a waste line 40 connected to the port 7 of the sample valve 11 of the second analysis unit.

Branch 22 of the sample circulation circuit has been fitted with a solenoid valve 24 connected to the atmosphere, whose function is to bring the sample loop 19 to atmospheric pressure so as to have equivalent samplings and reproducible analysis cycles.

FIG. 2 shows also an air circuit. The air circuit is controlled by a primary pressure regulator 42 equipped with pressure gauge 44, and is shunted downstream of the primary pressure 42 in two equivalent circuits one for the first and one for the second analysis unit. Each of these two derived air circuits is fitted with a solenoid valve 25 to commute the assist air of the sample valve 11, and includes a branch 26 connected to the detector's flame ionisation combustion chamber to oxygenate the space in which the combustion of the hydrocarbon mixture brought from the carrier gas is to take place. Branch 26 of the air circuit, which brings air to the flame ionisation detector, is fitted with a pressure regulator 27 and a pressure gauge 28 for fine checking the feeding of the air to the detector.

Figure 3:
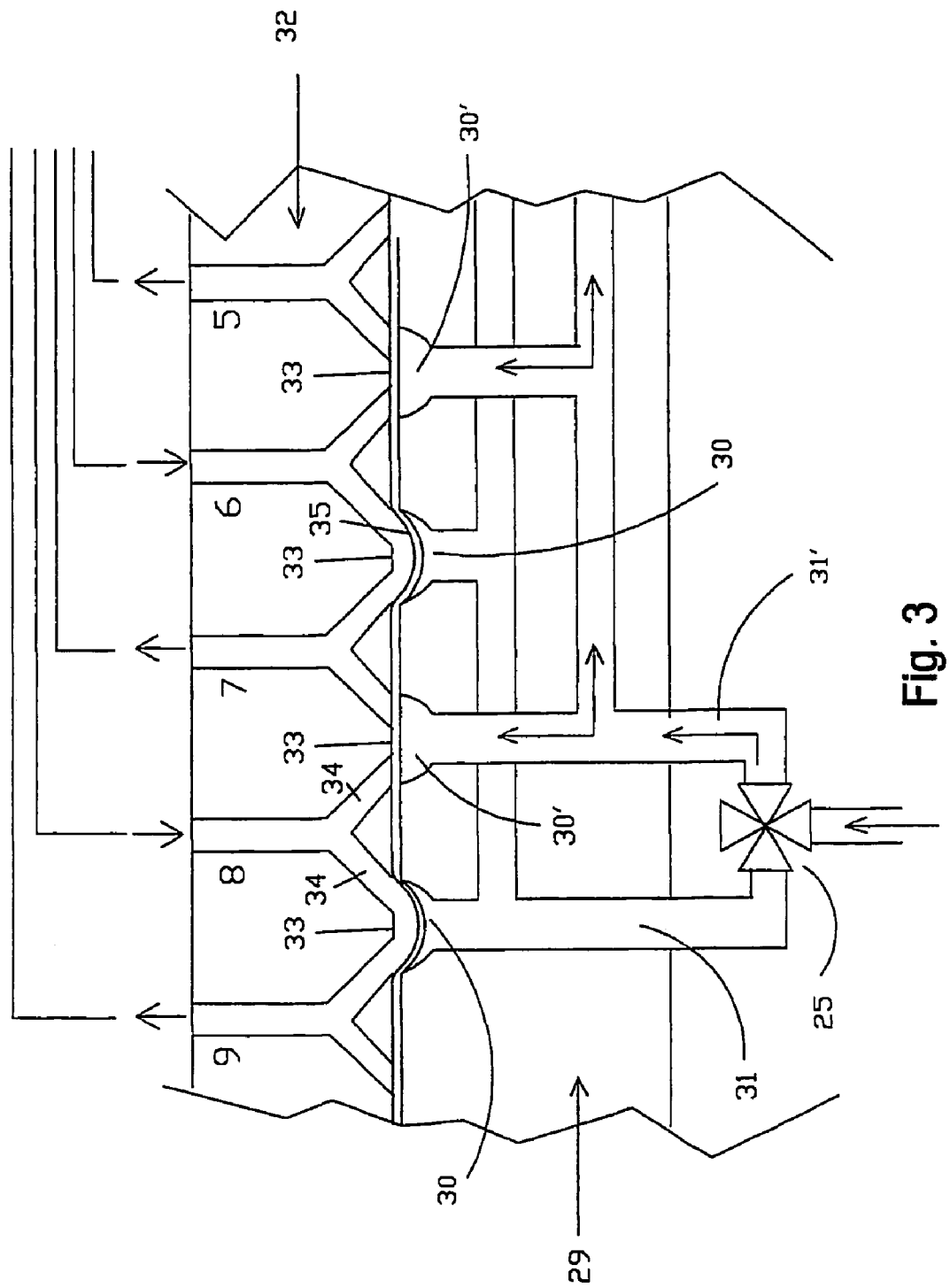
FIG. 3 is a magnified schematic view of a portion of the sampling valve present in the analytical double circuit of this invention.

With particular reference to FIG. 3 the structure and functioning of the sample valve 11 are now described.

Sample valve 11 is composed of two metal blocks separated by an elastic membrane 35.

The bottom block 29 constitutes the valve's command section. It is composed of ten semi-spherical cells ordered by circumference and grouped in fives in cell groups 30 and 30' respectively so that each cell of a group is alternatively placed next to a cell of the other group. The cells of each group are in fluid communication between each other and every group of cells 30 and 30' is in turn in liquid communication with a corresponding control circuit 31 and 31' connected to a corresponding exit of the solenoid valve 25 which commutes servo control air of the sample valve 11.

The top block 32 provides semi-spherical valves 33 each with two holes 34 connected in a "Y" shape with holes 34 contiguous to cells 30 and 30' adjacent. The ten resulting circuits are brought back to the head of the top block to create the ten ports of the sample valve 11.

Depending on the state of the solenoid valve commuting the servo control's air 25 the air under pressure supplies alternatively one of the two control circuits 31 or 31' putting under pressure one group of cells 30 or 30' whilst the other group of cells 30' or 30 remains at atmospheric pressure. The air present in each cell of the groups of cells under pressure flexes the membrane 35 which is pushed to cling to the semi-spherical valve 33 found on top of the cells which are under pressure until the passage between the two holes 34 of those semi-spherical valve 33 are hermetically closed.

In the commuting state of the sample valve shown in FIG. 3 the port couples 6 and 7, 8 and 9 are in communication whereas the passage between the ports couples 5 and 6, 7 and 8 is hermetically closed.

Commuting the solenoid valve of the servo control's air cells 30 or 30' previously at air pressure are brought to atmospheric pressure and vice versa the cells previously at atmospheric pressure are pressurised.

The functioning of the gas chromatograph object of this invention is as follows.

Every analysis cycle of the double analytical cycle is divided in two successive phases of which the first is called sampling pre-cut and the second analysis/back purging.

The first analysis unit is calibrated to carry out in a set time, not above 60 seconds, an analysis cycle of methane components (C1) and ethane components (C2) of the sampled hydrocarbon mixture.

The second analysis unit is calibrated to carry out simultaneously in the same amount of time an analysis cycle of the heavier hydrocarbons, such as propane (C3), isobutane (iC4), normalbutane (nC4), isopentane (iC5) and normalpentane (nC5).

The machine's calibration regarding the hydrocarbon components of the mixture is multi-point, namely that calibration is carried out on different scales making the machine analyse a constant and reproducible volume of gas mixtures composed of one or more hydrocarbon components at known concentration.

By way of an example here is a possible multi-point calibration in which only the methane (C1) is calibrated on three different scales, since usually it is precisely in the volumetric concentration of the methane (C1) component of the samples analysed that major fluctuations occur: in the 0-100% vol scale the machine's calibration is carried out on a mixture of 50% vol methane (C1) and 50% vol of air; in the 0-10% scale calibration is carried out on a mixture of 9% vol of methane (C1), 1,5% vol of ethane (C2), 1,5% vol of propane (C3), 1,5% vol of isobutane (iC4), 1,5% vol of normalbutane (nC4), 0,7% vol of isopentane (iC5), 0,7% vol of normalpentane (nC5), and air; in the 0-1% vol scale calibration is carried out on a mixture of 0,5% vol of methane (C1) and air.

The machine's calibration obviously gives the retention times of the single hydrocarbon components.

The preparation of the analysis cycle of the two analysis units starts by establishing, under equal analysis cycle time conditions of the two analysis units, the duration of the first and second phase which compose the analysis cycle: this preparation is carried out by regulating for the two analysis units separately the gas carrier's capacity and/or the length of the first separation column. As mentioned above, the gas carrier's capacity must be always kept constant in order to ensure the reproducibility of the migration times of the various components of the gas mixture being analysed.

The analysis cycle of each analysis unit is made up of, as mentioned above, two phases essentially, one called sampling/pre-cut the other analysis/back purging, to which the two commuting states of the sample valves correspond.

The first phase of the analysis cycle called sampling/pre-cut is associated to the commuting state of the sample valves 11 wherein the ports 1 and 2, 3 and 4, 5 and 6, 7 and 8, 9 and 10 are in fluid communication.

In the first phase of the analysis cycle shown in FIGS. 1a and 2, assuming the gas mixture sample to be analysed has already filled the sample loop 19, a part of the hydrogen flow coming from the first circulation branch flows successively through branch 13, collects the sample volume from the sample loop 19, flows through the first chromatographic separation column 18 where the various hydrocarbon components present in the sampled gas mixture will start to be separated, these components will then exit the separation column in increasing molecular weight order to then enter the second column. Part of the sample taken from the carrier (H2) can already reach the FID after having being fractionated further when crossing the second separation column 20 of the two analysis units. It is important to calculate the duration of this first phase in the two analysis units so that at its completion all and only the interesting components for this analysis will have exited the first sampling column, that is to say only methane (C1) and ethane (C2) for the first prima analysis unit, methane (C1), ethane (C2), propane (C3), isobutane (iC4), normalbutane (nC4), isopentane (iC5), normalpentane (nC5) for the second analysis unit. The remaining hydrogen flow flows in succession through compensation column 14 and goes to exit through line 21. During this first phase the sample coming from the external line 22 is not introduced in the sample loop but enters in the port 8 of the sample valve 11 of the first analysis unit, exits from port 7 of the sample valve 11 of the first analysis unit, flows through branch 23 which acts as bridge between the port 7 of the sample valve 11 of the first analysis unit and the port 8 of the sample valve 11 of the second analysis unit, and makes for the exit line 40 which starts from the port 7 of the sample valve 11 of the second analysis unit.

The second phase of the analysis cycle called back purging starts from the commuting of the sample valve 11 which now puts in liquid communication the ports 2 and 3, 4 and 5, 6 and 7, 8 and 9, 10 and 1.

In this second phase all the sample which has emerged from the first sampling column 18 at the end of the first phase of the analysis cycle is carried to the second separation column 20, where the hydrocarbon components are further fractionated, and from here it passes to the FID, the sample carrier being transported by a part of the hydrogen "carrier" coming from the compensation column 14. The compensation column 14 has identical structural characteristics to the first separation column 18 and guarantees that the hydrogen carrier experiences the same load loss of those experienced in the preceding phase during its passage through the first separation column 18.

In the first analysis unit's FID only the methane (C1) and ethane (C2) components will be detected. This will create two chromatographic peaks distanced in time and therefore easy to distinguish on the chromatogram elaborated by the electrometer of the first analysis unit.

In the second analysis unit's FID the methane (C1), ethane (C2), propane (C3), isobutane (iC4), normalbutane (nC4), isopentane (iC5), normalpentane (nC5) components will be detected. These will create five chromatographic peaks in to the chromatogram elaborated by the electrometer of the second analysis unit. The methane (C1) and ethane (C2) components analysed by the second analysis unit are not separated correctly and are therefore automatically rejected at the end of the analysis.

Also in the second phase of the analysis cycle, whilst the sample to be analysed is transported by a part of the hydrogen (H2) carrier to the FID, another part of the hydrogen (H2) carrier coming from line 13 goes in the opposite direction compared to the first phase the first separation column 18 in order to carry out a back purging wash of the first separation column 18 and therefore eliminate the hydrocarbon elements which have accumulated inside it at the end of the first analysis cycle phase, after which it proceeds to the exit through line 21.

During this second phase, the sample continues to flow through sample loop 19 and continues on towards the exit line 23.

Before the first phase of analysis/pre-cut takes place, the solenoid valve 24 placed on the feeding line of the sample is driven to open in order to bring the sample loop 19 to atmospheric pressure.

Since usually in the gas mixture to be analysed the lighter components such as methane and ethane can be present in high concentrations of many percentage volume units whereas heavier hydrocarbon components are present in modest concentrations close to one percentage volume unit, it is preferable to have two different measurement scales of the gas chromatograph for the first and second analysis units. Since the use of a highly sensitive electrometer in the second analysis unit would mean a rather high background noise of the electrometer, it is preferable to reduce the sensitivity of the electrometer of the second analysis unit and compensate the reduced electrometer's sensitivity by increasing the volume of the sample loop of the second analysis unit.

By way of an example the volume of the sample loop of the second analysis unit of this invention is approximately 20 times higher than that of the first sample loop.

By way of an example the sample loop of the first analysis unit is a small steel tube 10 cm long and with an internal diameter of 0,5 mm for a total volume of 20μ (microlitres), whereas the sample loop of the second analysis unit is a small steel tube 50 cm long and with an internal diameter of 1 mm for a total volume of 392μ.

The sampling carried out by the ten port membrane valve of small, constant and reproducible quantities of the sample to be analysed, quantifiable in tens of microlitres for the first analysis unit and in hundreds microlitres for the second analysis unit, helps to avoid saturation of the electrometer's signal of the two analysis units.

Figure 4:
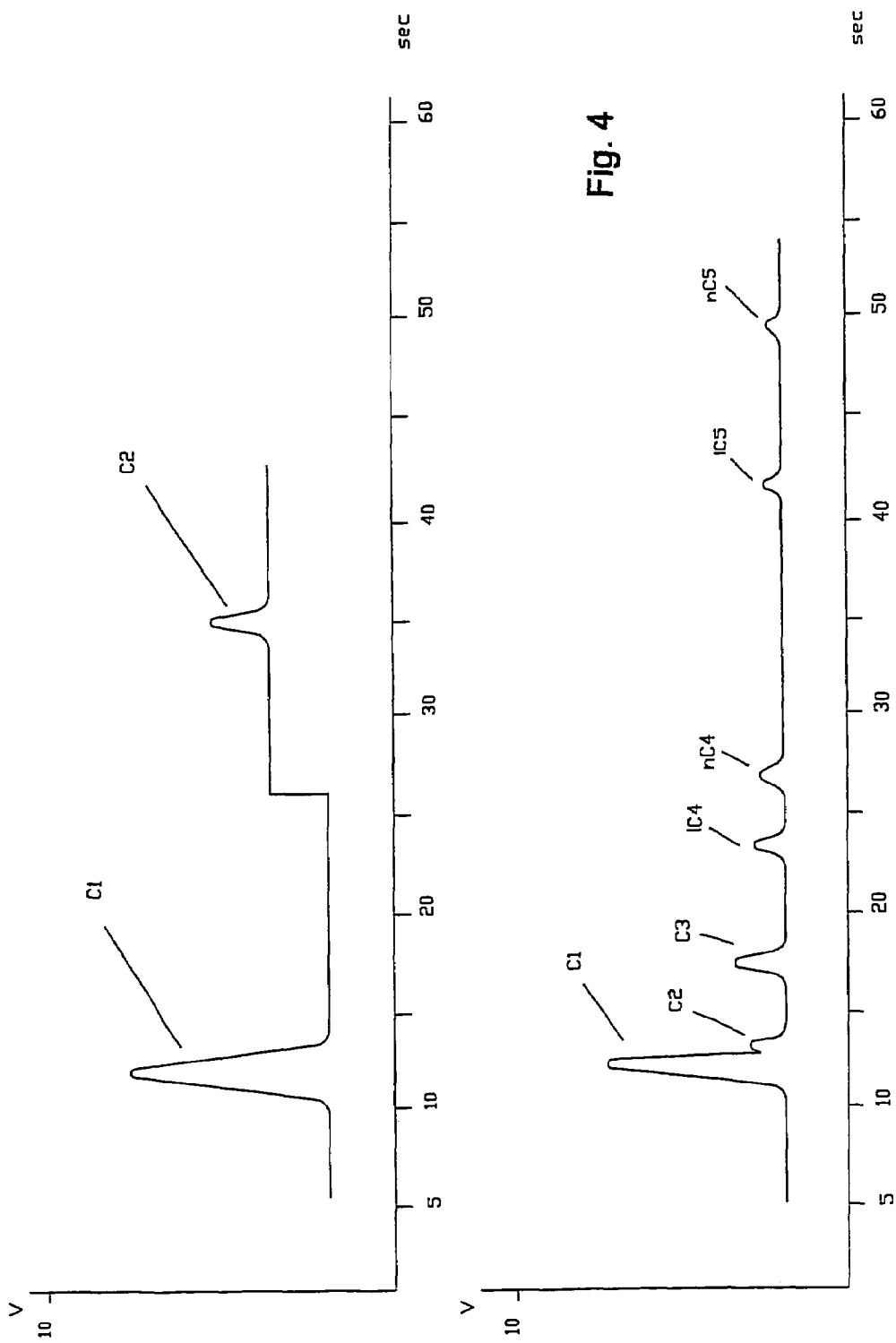
FIG. 4 is a chromatogram showing the result of a 60-second analysis cycle of a hydrocarbon mixture measured using the machine object of this invention.

Lastly, FIG. 4 shows the chromatogram resulting from an analysis carried out by the machine's double analytical circuit in conformity with this invention.

FIG. 4 above shows the chromatogram elaborated by the first analysis unit, in which a 25-second difference is highlighted between the readings of the methane (C1) and ethane (C2) chromatographic peaks. As the figure shows, thanks to this timing separation between the chromatographic peaks of methane and ethane it is possible to carry out an automatic variation of the sensitivity of the scale adopted by the electrometer to elaborate the chromatogram passing from the methane analysis to the ethane analysis (the increase of the scale's sensitivity can be seen clearly in FIG. 4 above by the "step" of the signal or by the electrometer's background noise).

FIG. 4 below shows the chromatogram elaborated by the second analysis unit in which the following chromatographic peaks are evident: methane (C1), ethane (C2), propane (C3), isobutane (iC4), normalbutane (nC4), isopentane (iC5), and normalpentane (nC5). Clearly that the methane (C1) and ethane (C2) chromatographic peaks overlap partially so that the evaluation of the area subtending them is difficult, this being due to the methane (C1) and ethane (C2) concentrations present in the sample analysed, as mentioned earlier. It would be possible to extrapolate the curve of the two chromatographic peaks in the superposition region using a mathematical function only by renouncing to the analysis' precision.

What is claimed is:

1. A field flame ionisation gas chromatograph for the analysis of a hydrocarbon gas mixture found in particular in mud from oil drilling and sampled by a gas carrier, characterised in that it comprises a first and a second analysis unit working in parallel simultaneously, said first analysis unit being dedicated exclusively to the analysis of methane and ethane, and said second analysis unit being dedicated to the analysis of propane, isobutane, normalbutane, isopentane and normalpentane.

2. A field gas chromatograph according to claim 1, characterised in that each one of said first and second analysis unit comprises a sample loop( 19), a first chromatographic separation column (18), a second chromatographic separation column (20), a chromatographic compensation column (14) identical to the first chromatographic column (18), a flame ionisation detector connected to the second separation column (20), an electrometer for the conversion of the electric power collected by the flame ionisation detector into a tension signal which traces a chromatogram, and a ten port pneumatic sampling valve (11) to commute the carrier gas circulation circuit.

3. A field gas chromatograph according to claim 1, characterised in that the analysis time of analysis carried out by the said analysis units is not above 60 seconds.

4. A field gas chromatograph according to claim 1, characterised in that hydrogen is used as carrier gas for the sample.

5. A field gas chromatograph according to claim 2, characterised in that the said sample loop (19) of the first analysis unit has a volume of a few tens of microliters.

6. A field gas chromatograph according to claim from 5, characterised in that said sample loop (19) of the second analysis unit has a volume of a few hundreds of microliters.

7. An analysis cycle of a gas chromatograph according to claim 2, characterised in that it comprises a first phase called sampling/pre-cut phase in which part of the carrier gas circulates through the sample loop (19) to transport the sample taken in the sample loop (19) to the first separation column (18), said first phase extending for a time such as to pre-cut at the exit of the first separation column (18) only the hydrocarbons to be analysed, and a second phase called analysis and back purging phase during which part of the carrier gas, after having crossed the compensation column (14), takes all the sample which has been pre-cut in the first phase of the analysis cycle at the exit of the first separation column (18) and convoys it to the flame ionisation detector while the other part of the carrier gas washes the first chromatographic column (18) by back purging.

8. An analysis cycle according to claim 7, characterised in that the methane and ethane components analysed in the second analysis unit are automatically eliminated at the end of the analysis.

9. An analysis cycle according to claim 7, characterised in that the sample to be analysed passes through the sampling loops (19) of the two analysis units in series during the second phase of the analysis cycle to fill up the sampling loops (19) of the two analysis units.

10. An analysis cycle according to claim 7, characterised in that the sampling loops (19) of the two analysis units are put at atmospheric pressure before the beginning of the first phase of the analysis cycle.

11. An analysis cycle according to claim 7, characterised in that the first analysis unit's electrometer changes scale sensitivity automatically passing from the analysis of methane to that of ethane.

12. An analysis cycle according to claim 6, characterised in that the sensitivity scale adopted for the second analysis unit's electrometer is inferior to the sensitivity scale adopted for the first analysis unit's electrometer.

13. A field gas chromatograph according to claim 2, characterised in that the analysis time of analysis carried out by the said analysis units is not above 60 seconds.

14. A field gas chromatograph according to claim 2, characterised in that hydrogen is used as carrier gas for the sample.

15. A field gas chromatograph according to claim 3, characterised in that hydrogen is used as carrier gas for the sample.

16. A field gas chromatograph according to claim 3, characterised in that the said sample loop (19) of the first analysis unit has a volume of a few tens of microliters.

* * * * *